US006572640B1

(12) United States Patent
Balding et al.

(10) Patent No.: US 6,572,640 B1
(45) Date of Patent: Jun. 3, 2003

(54) METHOD AND APPARATUS FOR CARDIOPULMONARY BYPASS PATIENT TEMPERATURE CONTROL

(75) Inventors: David P. Balding, Mission Viejo, CA (US); William J. Worthen, Coto de Caza, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/990,211

(22) Filed: Nov. 21, 2001

(51) Int. Cl.⁷ .................................................. A61F 7/00
(52) U.S. Cl. ........................................ 607/105; 607/106
(58) Field of Search ............... 607/96–106; 606/20–27; 604/113–114

(56) References Cited

U.S. PATENT DOCUMENTS

| | | |
|---|---|---|
| 2,308,484 A | 1/1943 | Auzin et al. |
| 3,125,096 A | 3/1964 | Antiles et al. |
| 3,142,158 A | 7/1964 | Podolsky |
| 3,238,944 A | 3/1966 | Hirschhorn |
| 3,282,267 A | 11/1966 | Eidus |
| 3,327,713 A | 6/1967 | Eidus |
| 3,425,419 A | 2/1969 | Dato et al. |
| 3,504,674 A | 4/1970 | Swenson et al. |
| 3,738,372 A | 6/1973 | Shioshvili |
| 3,776,241 A | 12/1973 | Magilton et al. |
| 3,897,790 A | 8/1975 | Magilton et al. |
| 3,913,581 A | 10/1975 | Ritson et al. |
| 4,010,795 A | 3/1977 | Stenberg |
| 4,111,209 A | 9/1978 | Wolvek et al. |
| 4,154,245 A | 5/1979 | Daily |
| 4,249,923 A | 2/1981 | Walda |
| 4,298,006 A | 11/1981 | Parks |
| 4,416,280 A | 11/1983 | Carpenter et al. |
| 4,416,281 A | 11/1983 | Cooper et al. |
| 4,427,009 A | 1/1984 | Wells et al. |
| 4,512,163 A | 4/1985 | Wells et al. |
| 4,546,759 A | 10/1985 | Solar |
| 4,583,969 A | 4/1986 | Mortensen |
| 4,672,962 A | 6/1987 | Hershenson |

(List continued on next page.)

FOREIGN PATENT DOCUMENTS

| | | |
|---|---|---|
| WO | WO 91/05528 | 5/1991 |
| WO | WO 98/26831 | 6/1998 |
| WO | WO 98/31312 | 7/1998 |

OTHER PUBLICATIONS

Levine, S., Medivance: Climate Control for the Body, Jul./Aug. 2001, In Vivo, vol. 19, No. 7 (reprinted enclosed).*
"Improving Outcome from Cardiac Arrest in the Hospital with a Reorganized and Strengthened Chain of Survival: An American View". Kaye et al. Resuscitation, 31:181–186. 1996.
"Resuscitative Hypothermia". Marion et al. Crit. Care Med., 24(2):S81–S89. 1996.
"Selective Brain Cooling After Cardiac Arrest". Safar et al. Crit. Care Med., 24(6):911–914. 1996.
"Review Induced Hypothermia in Intensive Care Medicine". Bernard. Anesthesia and Intensive Care, 24(3): 382:388. 1996.
"Clinical Trial of Induced Hypothermia in Comatose Survivors of Out–of–Hospital Cardiac Arrest". Bernard et al. Annals of Emergency Medicine, 30(2): 146–153. 1997.

Primary Examiner—Roy D. Gibson
(74) Attorney, Agent, or Firm—Arlyn L. Alonzo

(57) ABSTRACT

A cardiopulmonary bypass patient is precooled using an indwelling catheter. Cardiopulmonary bypass is initiated when a target temperature or range are achieved, as determined by automatic temperature feedback provided to a control module. The patient may also be rewarmed at a controlled rate during or after termination of cardiopulmonary bypass such that faster and safer termination is realized.

29 Claims, 3 Drawing Sheets

U.S. PATENT DOCUMENTS

| | | |
|---|---|---|
| 4,745,922 A | 5/1988 | Taylor |
| 4,748,979 A | 6/1988 | Hershenson |
| 4,750,493 A | 6/1988 | Brader |
| 4,754,752 A | 7/1988 | Ginsburg et al. |
| 4,759,349 A | 7/1988 | Betz et al. |
| 4,791,930 A | 12/1988 | Suzuki et al. |
| 4,813,210 A | 3/1989 | Masuda et al. |
| 4,823,076 A | 4/1989 | Haines et al. |
| RE32,983 E | 7/1989 | Levy |
| 4,844,074 A | 7/1989 | Kurucz |
| 4,850,958 A | 7/1989 | Berry et al. |
| 4,860,744 A | 8/1989 | Johnson et al. |
| 4,883,455 A | 11/1989 | Leonard |
| 4,897,082 A | 1/1990 | Erskine |
| 4,899,741 A | 2/1990 | Bentley et al. |
| 4,920,963 A | 5/1990 | Brader |
| 4,941,475 A | 7/1990 | Williams et al. |
| 4,987,896 A | 1/1991 | Nakamatsu |
| RE33,561 E | 3/1991 | Levy |
| 5,019,075 A | 5/1991 | Spears et al. |
| 5,021,045 A | 6/1991 | Buckberg et al. |
| 5,041,089 A | 8/1991 | Mueller et al. |
| 5,066,578 A | 11/1991 | Wikman-Coffelt |
| 5,078,713 A | 1/1992 | Varney |
| 5,092,841 A | 3/1992 | Spears |
| 5,098,376 A | 3/1992 | Berry et al. |
| 5,106,360 A | 4/1992 | Ishiwara et al. |
| 5,135,474 A | 8/1992 | Swan et al. |
| 5,139,496 A | 8/1992 | Hed |
| 5,147,355 A | 9/1992 | Friedman et al. |
| 5,147,385 A | 9/1992 | Beck et al. |
| 5,151,100 A | 9/1992 | Abele et al. |
| 5,158,534 A | 10/1992 | Berry et al. |
| 5,167,960 A | 12/1992 | Ito et al. |
| 5,174,285 A | 12/1992 | Fontenot |
| 5,182,317 A | 1/1993 | Winters et al. |
| 5,191,883 A | 3/1993 | Lennox et al. |
| 5,196,024 A | 3/1993 | Barath |
| 5,211,631 A | 5/1993 | Sheaff |
| 5,230,862 A | 7/1993 | Berry et al. |
| 5,248,312 A | 9/1993 | Langberg |
| 5,250,070 A | 10/1993 | Parodi |
| 5,257,977 A | 11/1993 | Eshel |
| 5,259,839 A | 11/1993 | Burns |
| 5,261,399 A | 11/1993 | Klatz et al. |
| 5,262,451 A | 11/1993 | Winters et al. |
| 5,269,758 A | 12/1993 | Taheri |
| 5,275,595 A | 1/1994 | Dobak, III |
| 5,279,598 A | 1/1994 | Sheaff |
| 5,281,213 A | 1/1994 | Milder et al. |
| 5,281,215 A | 1/1994 | Milder |
| 5,304,214 A | 4/1994 | DeFord et al. |
| 5,324,260 A | 6/1994 | O'Neill et al. |
| 5,324,286 A | 6/1994 | Fowle |
| 5,338,770 A | 8/1994 | Winters et al. |
| 5,342,301 A | 8/1994 | Saab |
| 5,342,693 A | 8/1994 | Winters et al. |
| 5,354,277 A | 10/1994 | Guzman et al. |
| 5,370,616 A | 12/1994 | Keith et al. |
| 5,382,234 A | 1/1995 | Cornelius et al. |
| 5,385,540 A | 1/1995 | Abbott et al. |
| 5,403,281 A | 4/1995 | O'Neill et al. |
| 5,411,477 A | 5/1995 | Saab |
| 5,423,807 A | 6/1995 | Milder |
| 5,437,673 A | 8/1995 | Baust et al. |
| 5,452,582 A | 9/1995 | Longsworth |
| 5,474,533 A | 12/1995 | Ward et al. |
| 5,478,309 A | 12/1995 | Sweezer et al. |
| 5,486,204 A | 1/1996 | Clifton |
| 5,486,208 A | 1/1996 | Ginsburg |
| 5,498,261 A | 3/1996 | Strul |
| 5,531,776 A | 7/1996 | Ward et al. |
| 5,545,134 A | 8/1996 | Hilaire et al. |
| 5,545,137 A | 8/1996 | Rudie et al. |
| 5,545,161 A | 8/1996 | Imran |
| 5,549,552 A | 8/1996 | Peters et al. |
| 5,549,559 A | 8/1996 | Eshel |
| RE35,352 E | 10/1996 | Peters |
| 5,562,606 A | 10/1996 | Huybregts |
| 5,609,620 A | 3/1997 | Daily |
| 5,624,392 A | 4/1997 | Saab |
| 5,655,548 A | 8/1997 | Nelson et al. |
| 5,656,420 A | 8/1997 | Chien |
| 5,693,080 A | 12/1997 | Wallstén et al. |
| 5,695,457 A | 12/1997 | St. Goar et al. |
| 5,700,828 A | 12/1997 | Federowicz et al. |
| 5,702,435 A | 12/1997 | Maytal |
| 5,716,386 A | 2/1998 | Ward et al. |
| 5,733,319 A | 3/1998 | Neilson et al. |
| 5,735,809 A | 4/1998 | Gorsuch |
| 5,755,756 A | 5/1998 | Freedman, Jr. et al. |
| 5,758,505 A | 6/1998 | Dobak, III et al. |
| 5,759,182 A | 6/1998 | Varney et al. |
| 5,776,176 A | 7/1998 | Rudie |
| 5,787,715 A | 8/1998 | Dobak, III et al. |
| 5,800,375 A | 9/1998 | Sweezer et al. |
| 5,800,486 A | 9/1998 | Thome et al. |
| 5,800,493 A | 9/1998 | Stevens et al. |
| 5,807,342 A | 9/1998 | Musgrave et al. |
| 5,807,395 A | 9/1998 | Mulier et al. |
| 5,833,624 A | 11/1998 | Rom et al. |
| 5,837,003 A | 11/1998 | Ginsburg |
| 5,861,021 A | 1/1999 | Thome et al. |
| 5,879,329 A | 3/1999 | Ginsburg |
| 5,902,268 A | 5/1999 | Saab |
| 5,902,274 A | 5/1999 | Yamamoto et al. |
| 5,902,299 A | 5/1999 | Jayaraman |
| 5,906,588 A | 5/1999 | Safar et al. |
| 5,957,917 A | 9/1999 | Doiron et al. |
| 5,957,963 A | 9/1999 | Dobak, III |
| 5,975,081 A | 11/1999 | Hood et al. |
| 6,126,684 A * | 10/2000 | Gobin et al. ................ 607/113 |
| 6,231,594 B1 * | 5/2001 | Dae ............................ 607/96 |
| 6,299,599 B1 * | 10/2001 | Pham et al. ................ 604/113 |
| 6,325,818 B1 * | 12/2001 | Werneth ..................... 607/105 |
| 6,491,039 B1 * | 12/2002 | Dobak, III .................. 128/898 |

\* cited by examiner

METHOD AND APPARATUS FOR CARDIOPULMONARY BYPASS PATIENT TEMPERATURE CONTROL

BACKGROUND OF THE INVENTION

1. Field of the Invention

The invention relates to cardiopulmonary bypass procedures, and more particularly, to controlling patient temperature in conjunction with said procedures.

2. Description of Related Art

Cardiopulmonary bypass surgery (CPB) is one of the most common surgical procedures performed in the United States. During CPB, the heart is stopped and the blood which normally returns to the right side of the heart passes through a pump and oxygenating system and is returned to the aorta, thereby bypassing the heart and lungs.

Primary goals of cardiopulmonary bypass for heart surgery are to provide life-support functions, a motionless, decompressed heart, and a dry, bloodless field of view for the surgeon. In a basic heart-lung life-support system oxygen-poor blood is diverted from the venous circulation of the patient and is transported to the heart-lung machine where reoxygenation occurs, carbon dioxide is discarded and heat regulation (warming or cooling) is accomplished. This processed blood is then returned (perfused) into the patient's arterial circulation for distribution throughout the entire body to nourish and maintain viability of the vital organs.

Although a common procedure (in excess of 400,000 open heart procedures per annum are conducted in North America) and although tremendous strides have been made so that open heart surgery is safer for patients, the procedure is not without its dangers. Further, while the vast majority of patients have marked improvement in their cardiac functional status following their procedure, of concern is the potential for damage to other organ systems which can result from the CPB procedure.

Particularly, time on bypass is positively and independently correlated to adverse outcome of CPB, and reducing pump time is a clinically meaningful measure of device performance. Neurocognitive deficits are associated with CPB and attributed to emboli in the arterial circulation inevitably associated with arterial cannulation, surgical procedures and large, complex extracorporeal devices.

Neurologic and other embolic related sequelae are typical for surgery where CPB is used. The reason for these problems is that emboli from various sources are launched into the arterial circulation as a result of extracorporeal circulation and procedures inside the heart. These emboli are in the arterial circulation and pass into the major organ systems throughout the body, without benefit of capture by the lungs. Emboli larger that blood cells (8–15 microns) lodge in the arterioles and capillaries and cause ischemic areas corresponding to the areas perfused by the occluded blood vessel.

Conventionally, various means are employed to either prevent the formation and release of emboli into the arterial blood circulation or filter or trap blood-borne emboli prior to infusion into the patient's arterial circulation. Examples of filters and traps are screen or depth type filters in the extracorporeal blood circuit. These filters or traps may be in reservoirs, integral to blood gas exchange devices (oxygenators), cardiotomy reservoirs, and arterial line filters. Antithrombotic coatings may be applied to extracorporeal devices and cannulae to prevent thromboemboli. Carbon dioxide flushes may be used to displace air (carbon dioxide is much more soluble in blood than air) from extracorporeal circuits and reduce the potential for air bubbles. Not withstanding the above measures, emboli and the associated neurologic sequelae are a feature of CPB.

Filtration methods for removing emboli from blood are limited by the cellular nature of blood and the blood's propensity to form thrombi when exposed to artificial surfaces and/or shear forces. As a filter's pore size approaches that of the blood cells (8–15 microns) the pressures needed to achieve sufficient flow are increased or the area of the filter must be increased to impractically large size. Additionally, as the shear forces adjacent to artificial surfaces increase, platelet aggregates and/or fibrin thrombi formation ensue on the downstream side of the filter and, paradoxically, create blood emboli.

Actions and manipulations of the patient and equipment for CPB cause emboli in the arterial blood flow. It has not been possible to practically eliminate all the emboli so caused. For example, insertions of the venous and arterial cannulae cause small pieces of cut or torn tissue to enter the blood. Cardiotomy suction blood (typically filtered and returned to the CPB circuit) has air, fat and tissue emboli that can only be partially filtered (for reasons previously mentioned) out of the blood before going into the arterial circulation. As part of CPB, large clamps are applied and released at various times to stop/start blood flow in major blood vessels and this action causes damage to the blood vessel lumen and creates stagnant, clot prone areas near the clamp. Subsequent movement and eventual release of clamps has been shown to launch measurable emboli into the arterial (including cerebral) circulation.

Cooling the patient is routinely employed in CPB. This is accomplished by heat exchangers in the extracorporeal circuit. The benefits of cooling to protect the patient from ischemic insult are well recognized. However, conventionally the patient is at normal temperature at the time that CPB is initiated and no cooling protection is afforded until after the initial embolic insult. 10–20 minutes may be required after the start of CPB to reach the desired hypothermic temperature. Significant emboli (tissue, particulate, air and thrombus) are released at the precise time that CPB is initiated and the patient has not yet cooled below the normothermic range (36.0–37.5° C.).

Cooling also provides the benefit of increasing the margin of safety in case of equipment failure, whereby patient metabolism is reduced by the cooled blood being reintroduced into the body, in turn reducing the body's need for oxygen and the tolerance for its deprivation in the event of such failure. Specifically, an 8–10% decrease in oxygen consumption is correlated with each degree (Celcius) drop in body temperature. Thus it is not uncommon to lower patient core body temperature to about 32° C., or even lower, during CPB.

BRIEF SUMMARY OF THE INVENTION

The present invention relates to methods and systems for controlling patient temperature during cardiopulmonary bypass surgery. In one embodiment, a patient undergoing cardiopulmonary bypass surgery is precooled using an indwelling catheter inserted into the central venous system of the patient. The indwelling catheter operates to cool the patient, lowering core body temperature before cardiopulmonary bypass is initiated. A pre-determined patient target temperature can be set so that cooling is terminated or patient target temperature is automatically maintained when the target temperature is reached.

In a second embodiment, the indwelling catheter can be used to control the rate of patient rewarming once the cardiopulmonary bypass surgery is near or at completion. Controlled rewarming can be encompassed by applying heat to the patient's blood flow using the indwelling catheter. Additionally, the caregiver can control the rate at which the patient is rewarmed by selecting the pump speed and bath temperature of the temperature control module.

It is the object of the present invention to provide a systemic heat exchange method and system that are effective, are easy to use and require minimal added work for medical personnel. Additional objects and advantages of the invention will be set forth in part in the description which follows, and may be obvious from the description or learned by practice of the invention. The objects and advantages of the invention also may be realized and attained by means of the method acts, instrumentalities and combinations particularly pointed out in the appended claims.

BRIEF DESCRIPTION OF THE SEVERAL VIEWS OF THE DRAWING(S)

Many advantages of the present invention will be apparent to those skilled in the art with a reading of this specification in conjunction with the attached drawings, wherein like reference numerals are applied to like elements and wherein:

FIG. 3 is a is a cross-sectional view taken along line 3—3 of FIG. 2a; and

DETAILED DESCRIPTION OF THE INVENTION

Figure 1:
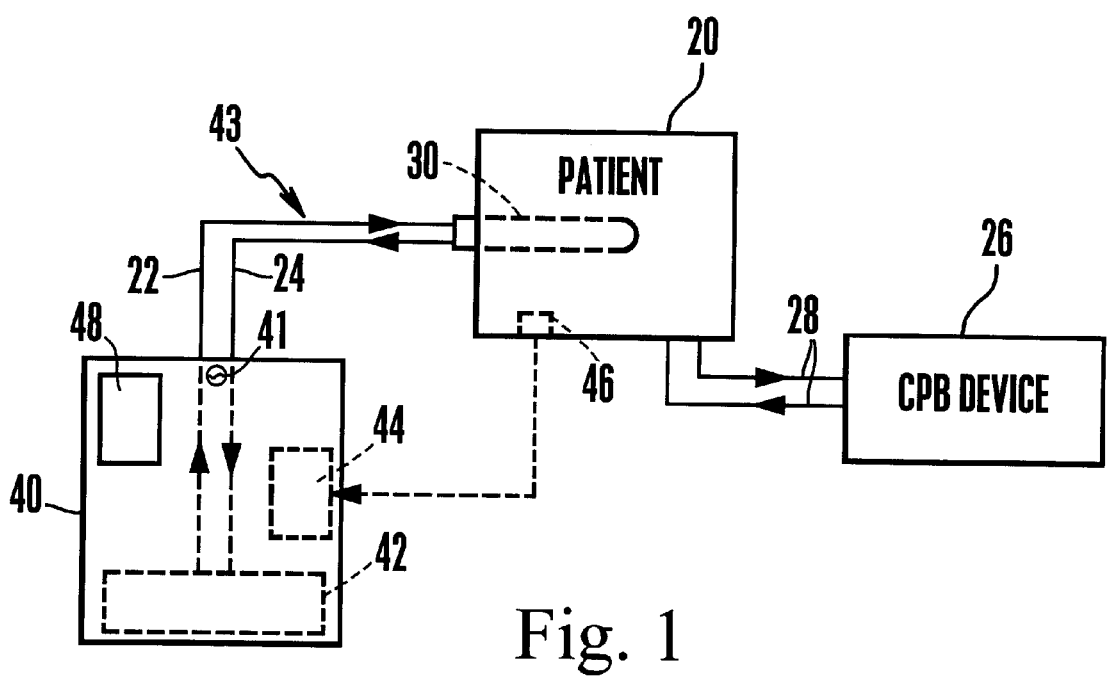
FIG. 1 is a schematic diagram showing temperature control in accordance with the invention.

FIG. 1 shows an arrangement in accordance with the present invention. A patient 20 is schematically depicted undergoing cardiopulmonary bypass (CPB) surgery using a CPB device 26, wherein patient blood is conveyed to and from the CPB device via a tube set 28. During CPB, device 26 operates to provide life-support functions, a motionless, decompressed heart, and a dry, bloodless field of view for the surgeon. In a basic heart-lung life-support system oxygen-poor blood is diverted from the venous circulation of the patient 20 and is transported to CPB device 26 where reoxygenation occurs, carbon dioxide is discarded and heat regulation (warming or cooling) is accomplished. This processed blood is then returned (perfused) into the patient's arterial circulation for distribution throughout the entire body to nourish and maintain viability of the vital organs.

Figure 2:
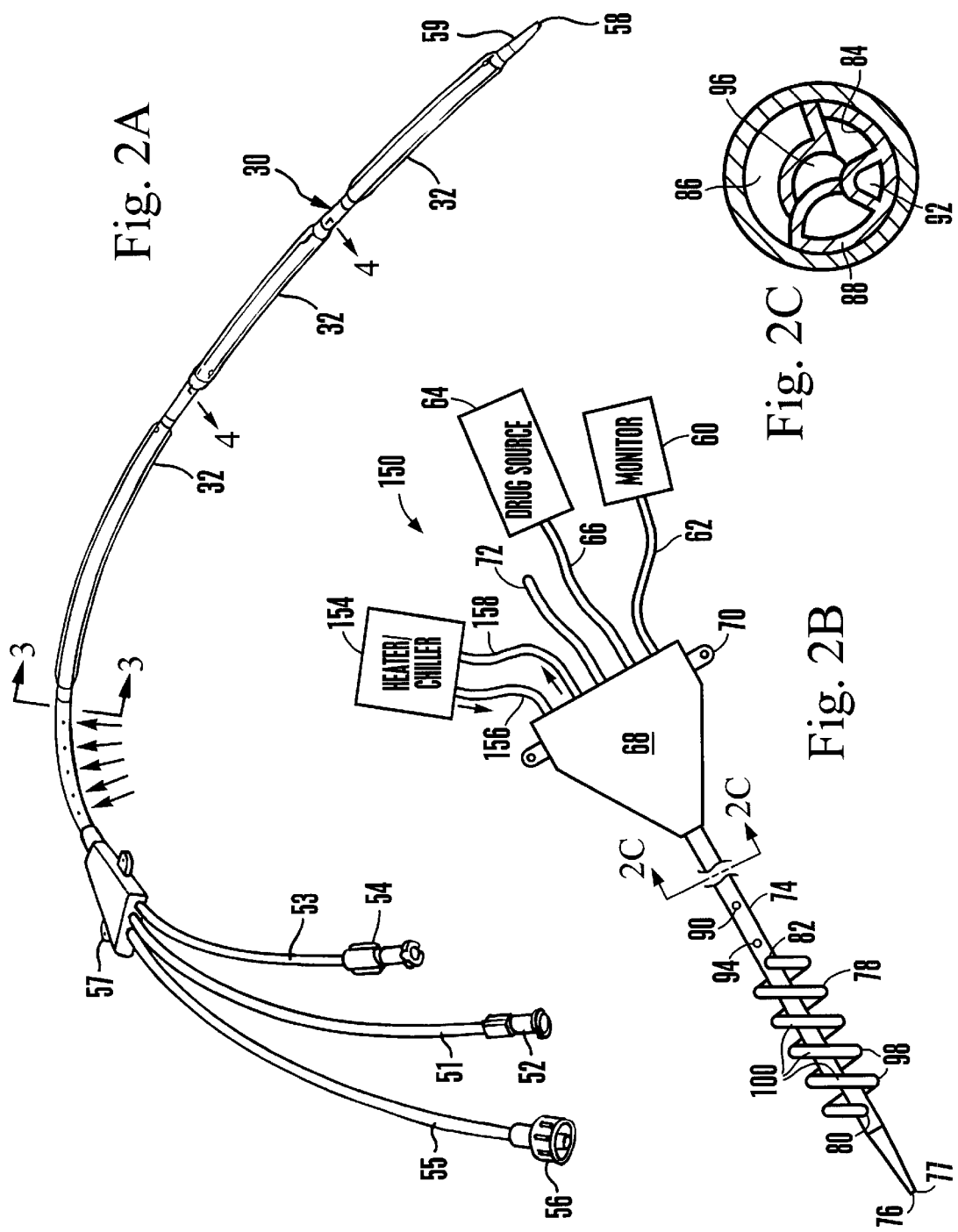
FIG. 2a is a perspective view of a catheter in accordance with the invention.
FIG. 2b is a perspective view of another catheter in accordance with the invention.
FIG. 2c is a cross-sectional view taken along line 6—6 of FIG. 2b.

FIG. 1 also shows a catheter 30 implanted in patient 20. Catheter 30, discussed in greater detail with reference to FIG. 2 below, is implanted in the patient and serves to remove heat from, or add heat to, the patient's blood flow in accordance with a temperature control device 40. Catheter 30 is in thermal communication with control unit 40 which regulates the core body temperature of patient 20 by controlling the temperature of the catheter. Thermal communication between catheter 30 and control unit 40 can be effected in a variety of ways. Preferably, a heat exchange fluid circuit 43 is used, wherein fluid is circulated through catheter 30 in a closed loop which includes intake and outflow tubes 22 and 24, respectively. Pump 41 provides the force for circulating the heat exchange fluid. The heat exchange fluid in fluid circuit 43 is in heat exchange relationship with a water bath 42 of control unit 40. The temperature of water bath 42 is controlled in accordance with an output from a temperature control module 44, which module receives patient core body temperature information from a probe 46. Control unit 40 contains a cooler (not shown) for cooling water bath 42. Control unit 40 may also contain a heater (not shown) for heating the water bath 42. Heating may also be accomplished using an electrical resistance heating element (not shown) or other means disposed on catheter 30.

Although depicted as occupying a location in the patient which is different from that of catheter 30, probe 46 may in fact be disposed on the catheter and therefore lie in the same location—that is, it may be disposed within a region of venous blood circulation, the preferred location of catheter 30 as discussed in further detail below. It is preferred, however, that probe 46 be of the bladder, esophagial, rectal or tympanic type.

Temperature control module 44 preferably includes a programmable processor (not shown) which receives input from an operator through an input device such as keypad 48. Using keypad 48, the operator can input various parameters for the operation of control unit 40. One such parameter is a targeted patient core body temperature level, which, in a precooling operation, may be about 32° C. To achieve this core body temperature, water bath 42 operates to cool the circulating fluid to about 4° C.

Figure 3:
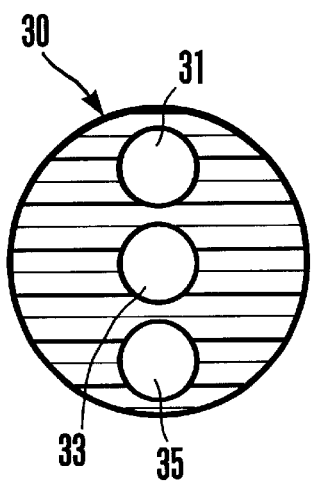

FIGS. 2a and 3 show in greater detail an exemplary arrangement of catheter 30 in accordance with the invention, with FIG. 3 being a cross-sectional view taken along lines 3—3 in FIG. 2a. Catheter 30 is an essentially tubular structure of about 8.5 French diameter. Catheter 30 includes a heat exchange region, such as one or more exterior balloons 32 in fluid communication with internal lumens 31 and 35 formed in the catheter. At the proximal end of catheter 30, lumens 31 and 35, along with a central lumen 33, extend into tubes 51, 53 and 55, which tubes are provided with appropriate fittings 52, 54 and 56 for connection to suitable devices (not shown). A suture anchor 57, from which tubes 51, 53, and 55 emerge, may be provided for anchoring catheter 30 to the patient 20 during operation. One or more radiopaque markers (not shown) may also be provided to aid with catheter visualization, or the tubular structure of the catheter, which is made of biocompatible material such as biocompatible polyurethane, may be impregnated with radiopaque material, such as barium sulfate. Depth markers (not shown) may also be provided to aid in insertion and manipulation.

Central lumen 33 provides a conduit for passage of a guidewire (not shown) through catheter 30. The guidewire, which is typically about 0.032 to 0.035 inches in diameter, may be used as in conventional practice to guide the catheter 30 through the patient's body to the appropriate location during initial introduction of the catheter. To that end, central lumen 33 communicates with the exterior of catheter 30 through fitting 54 at the proximal portion, and through aperture 58 at the distal portion, or tip 59, of catheter 30. Central lumen 33 may also be used to provide a conduit for passage of infusate to the body, or for removal of fluid such as blood therefrom.

Side lumens 31 and 35 are contiguous with fluid circuit 43 (FIG. 1), providing fluid flow paths for heat exchange fluid to circulate in catheter 30. Lumen 31 is an inflow lumen, extending through tube 51 to communicate with tube 22 of circuit 43. Lumen 35 is an outlflow lumen, extending through tube 55 to communicate with tube 24 of circuit 43. Thus fluid in circuit 43 enters catheter 30 through lumen 31 and exits catheter 30 through lumen 35.

Figure 4:
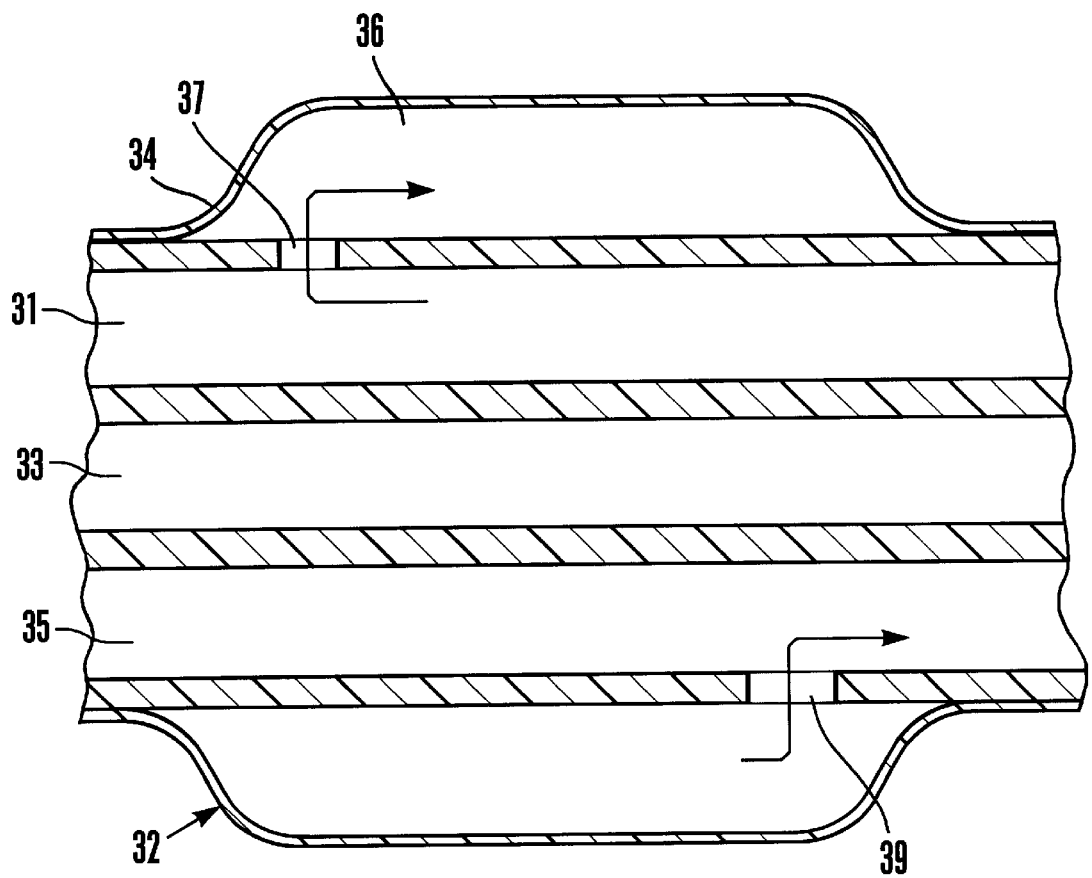
FIG. 4 is a sectional view of a catheter balloon in accordance with the invention.

With reference to FIG. 4, balloons 32 are formed exteriorly of catheter 30 and each comprise a tubular sheet of pliant material 34, such as extruded polymer, which is sealed at both ends against the exterior body structure of catheter 30, such that a cavity 36 bounded by the catheter and the tubular sheet of pliant material is formed. Inflow lumen 31 communicates with cavity 36 through a supply port 37, whence heat exchange fluid enters balloon 32 and causes the balloon to inflate. The fluid circulates through balloon 32, and exits at return port 39 into outflow lumen 35. When inflated, the diameter of each of balloons 32 expands to about 5–8 mm.

In another embodiment of a catheter 150, as shown in FIGS. 2b and 2c, at least two central venous components can be in communication with the catheter 150 for undertaking central venous functions in addition to controlling the temperature of the patient. These functions include and are not limited to drug infusion, blood extraction and blood pressure monitoring. For instance, a blood monitor 60 can communicate with the catheter 150 via a line 62 to monitor blood pressure or withdraw blood from the central venous system of the patient. Also, a drug source such as a syringe 64 can engage the catheter 150 via a connector with line 66 for infusing drugs or other medicament into the patient. The components 154, 60 and 64 can all be connected to the catheter 150 via a proximal connector hub 68 of the catheter 150. The hub 68 can be formed with a suture anchor 70 or other anchor structure such as tape for providing a means to fasten the catheter 150 to the skin of the patient for long-term use. Also, a guide wire lumen tube 72 may be engaged with the hub 68 and extend therethrough to a guidewire lumen.

Turning to the catheter 150, a preferably plastic, flexible catheter elongate body 74 extends distally away from the hub 68. The body 74 is biocompatible, and can be coated with an anti-microbial agent and with an anti-clotting agent such as heparin. The body 74 can be a unitary piece of hollow plastic or it can be made of more than one coaxial tube. Distally bonded to a portion or the body 74 is a comparatively more rigid frusto-conical shaped guide head 76, an open distal end of which can establish a distal infusion port 77.

A flexible, collapsible, helical-shaped heat exchange elongate element 78 surrounds the body 74. The heat exchange element 36 can be made of a plurality of discrete turns that are formed separately from each other and then joined together to communicate with each other. However, in a more preferred embodiment more easily fabricated, the elongate element 78 is a single, unitary tube made of very thin catheter balloon material that extends from a first end 80 to a second end 82 and the element 78 includes a heat transfer lumen extending longitudinally therethrough. The heat transfer lumen is in fluid communication with an input lumen 84 which is in turn in communication with the supply line 56. The heat transfer lumen of the element 78 is also in communication at the second end 82 with an output lumen 86 communicating with the return line 58. The elongate element 78 is in communication with the output lumen 86 at the second end 82. Thus, working fluid flows distally through the input lumen 84, into the helical transfer lumen of the elongate element 78, and then proximally back through the element 78 and the output lumen 86. In a separate embodiment, the working fluid flows proximally through the input lumen 84, into the helical transfer lumen of the elongate element 78, and then distally back through the element 78 and the output lumen 86.

In addition to the input lumen 84 and output lumen 86, the catheter 150 may have two or more infusion lumens which may be operated simultaneously with the control of the patient's temperature. Specifically, the first infusion lumen 88 terminates at a medial outlet port 90 and a second infusion lumen 92 terminates at a separate outlet port 94. Both lumens 88 and 92 are separated from the heat transfer fluid and both extend to the hub 68. A guide wire tube 96 communicates with the tube 72 extends to the distal port 78. These several passages provide communication for the introduction of medicine, the sampling of blood, the sensing of temperature and other purposes requiring access into the body passageway. The ports are shown separated to preclude mixing of drugs in the blood stream. In another embodiment, port 94 is distally located from the elongated element 78.

Looking specifically to the elongate element 78, a plurality of turns 98 are shown to define the helix which extends longitudinally of the elongate body 74. The turns 98 are bonded along a fraction of the length of each turn at locations 100 and are otherwise displaced from the body 74. This allows body fluid flow between the turns 98 and the body 74. Again, the turns 98 are of thin-walled, flexible material. The material need only retain the working fluid and may collapse under fluid pressure of the body fluid when the heat transfer lumen is at atmospheric pressure.

In accordance with the invention, a patient about to undergo cardiopulmonary bypass is precooled such that the patient's core body temperature is lowered in advance of bypass. First, catheter 30 is implanted into the patient. A preferred location is the central venous system, in order to maximize heat exchange with the patient's blood by exposing a volumetrically significant amount of blood to the catheter, and particularly, to balloons 32 thereof. Access to the central venous system can be gained through the subclavian or jugular veins, into the superior vena cava, or through the femoral vein into the inferior vena cava.

The indwelling catheter 30 operates to cool the patient, lowering core body temperature before cardiopulmonary bypass is initiated. A predetermined target temperature or temperature range, and possibly a cooling rate, are set by an operator, who inputs the temperature or temperature range to temperature control module 44 of control unit 40 using keypad 48. Temperature control module 44 monitors patient core body temperature using feedback from probe 46, and automatically adjusts the temperature in water bath 42, and in the circulating cooling fluid, to thereby conform to the target temperature or range. It will be noted that the speed of pump 41 can additionally or alternatively be controlled in order to adjust patient core body temperature.

Typically, precooling is conducted in the operating room and can commence about 15 minutes to one hour before cardiopulmonary bypass, which is typically the length of time required to bring core body temperature down to a target temperature or range of about 32° C. to 34° C. It is envisioned, however, that precooling can take place in the field, using portable equipment, particularly in the event of an emergency.

It is preferred that the precooling using catheter 30 occur before extracorporeal circulation is initiated. Thus it is contemplated that the precooling, preferably to the target temperature or range, take place before blood pumps (not shown) in CPB device 26 are turned on and the process of bypassing the patient's heart and lung functions takes place. It may also be appropriate to conduct precooling even earlier, such as before cannulation of the patient in preparation for bypass. The details of the precooling operation will of course be dictated by the particular circumstances, based on factors such as patient condition, location, etc.

An exemplary precooling process in accordance with the invention may take place as follows:

1. Patient begins anesthesia/ventilator in the operating room;
2. Catheter 30 is inserted into inferior vena cava of patient via the femoral vein, and cooling, preferably at the maximum rate wherein heat exchange fluid temperature of about 4° C. is used, commences in the direction of the target temperature or range;
3. Following, or in parallel to, active cooling using catheter 30, the patient's chest is opened and all the normal activities in preparation for normal cannulation for heart/lung bypass are conducted;
4. If needed, appropriate shivering control measures, including Demorol,™ can be used; and
5. Cooling can be stopped when patient core body temperature reaches the target temperature or range, or when normal heart/lung bypass commences, preferably whichever occurs first.

The invention is also directed to providing post CPB temperature control. Termination of CPB involves various procedures and associated risks. Some of these procedures are release of the cross clamp (not shown) used in diverting the patient's blood flow, and performing the gradual "weaning off" process. Weaning off of bypass involves gradually restoring normal heart function, by flushing the heart and washing off the potassium used to stop beating, and by rewarming the heart and subsequently discontinuing the pumping function of CPB device 26. In accordance with the invention, some or all of these procedures are performed at a temperature of about 32° C. to 34° C., facilitated by the use of indwelling catheter 30 and control unit 40 since at this juncture CPB bypass will have been or will be in the process of termination. Importantly, this ensures that the patient is at a temperature that is neuroprotective when the inevitable embolic shower associated with release of the cross clamp and weaning off bypass occur.

Further in accordance with the invention, catheter 30 and control unit 40 are used to provide a controlled rate of patient rewarming, for instance retarding this rate as desired, again to prolong the effects of cooling and maximize their benefits depending on the circumstances. Rewarming rate can be selectable such that operator enters this rate into temperature control module 44 of control unit 40, using keypad 48. This rate would preferably govern the rate of change of cooling, and particularly, the decrease in cooling, of heat exchange fluid in fluid circuit 43 and catheter 30 by water bath 42.

Controlled rewarming in accordance with the invention can also encompass applying heat to the patient's blood flow using catheter 30. This would of course accelerate rewarming and would save time by allowing removal of CPB and performance of post CPB procedures, such as closing the chest, in parallel with warming by catheter 30.

In accordance with the invention, the catheter 30 can be provided with instructions for use with precooling or rewarming of a cardiopulmonary patient as described above. In this manner, the catheter can be vended as a kit of parts which may include these instructions, along with for example the attendant tubing sets, fittings, and possibly, the control module 40 and other componentry necessary for practice of the invention. Although the precooling and rewarming processes have been described using catheter 30, these processes can just as well be implemented using catheter 150 as described herein.

The above are exemplary modes of carrying out the invention and are not intended to be limiting. It will be apparent to those of ordinary skill in the art that modifications thereto can be made without departure from the spirit and scope of the invention as set forth in the following claims.

What is claimed is:

1. A method for treating a patient comprising:
   reducing the core body temperature of the patient below normal body temperature by placing a catheter in a blood flow path of the patient and transferring heat from the blood in the blood flow path to the catheter; and
   initiating cardiopulmonary bypass of the patient when the core body temperature of the patient is below normal body temperature.

2. The method of claim 1, wherein the core body temperature of the patient is reduced to about 32° C.

3. The method of claim 1, wherein reducing the core body temperature of the patient further comprises:
   determining the core body temperature; and
   controlling the rate of heat transfer from the blood in the blood flow path to the catheter based on the determination of core body temperature.

4. The method of claim 1, wherein the catheter is placed in the central venous system of the patient.

5. The method of claim 1, wherein transferring comprises circulating in the catheter a heat exchange fluid having a temperature below the temperature of the blood in the blood flow path.

6. The method of claim 5, wherein circulating comprises:
   inflating one or more balloons of the catheter; and
   circulating the heat exchange fluid in the inflated one or more balloons.

7. The method of claim 5, wherein the temperature of the heat exchange fluid is about 4° C.

8. The method of claim 5, wherein reducing the core body temperature of the patient further comprises:
   determining the core body temperature; and
   controlling the rate of heat transfer from the blood in the blood flow path to the catheter based on the determination of core body temperature.

9. The method of claim 8, wherein controlling comprises selectively removing heat from the heat exchange fluid.

10. The method of claim 1, further comprising:.
    terminating cardiopulmonary bypass when the core body temperature of the patient is below normal body temperature.

11. The method of claim 10, wherein terminating comprises weaning off of bypass.

12. The method of claim 10, wherein terminating comprises discontinuing a blood pumping function of cardiopulmonary bypass.

13. The method of claim 10, wherein terminating comprises removing a cross clamp associated with cardiopulmonary bypass.

14. The method of claim 10, wherein terminating comprises removing a cannula associated with cardiopulmonary bypass.

15. The method of claim 10, wherein terminating comprises closing the chest of the patient.

16. The method of claim 10, wherein terminating is conducted when the core body temperature is about 32° C.–34° C.

17. The method of claim 10, further comprising:
increasing the core body temperature of the patient at an operator selected rate.

18. A method for treating a patient comprising:
performing cardiopulmonary bypass of the patient, including lowering the body temperature of the patient to below normal body temperature;
terminating cardiopulmonary bypass of the patient at a core body temperature below normal body temperature; and
during or after terminating cardiopulmonary bypass, selectively adding heat to the patient to thereby raise the core body temperature of the patient, wherein at least one of: the act of lowering the body temperature, and the act of selectively adding heat to the patient, is undertaken at least in part by placing a catheter in a blood flow path of the patient, and transferring heat between the catheter and the blood in the blood flow path.

19. The method of claim 18, wherein terminating comprises weaning off of bypass.

20. The method of claim 18, wherein terminating comprises discontinuing a blood pumping function of cardiopulmonary bypass.

21. The method of claim 18, wherein terminating comprises removing a cross clamp associated with cardiopulmonary bypass.

22. The method of claim 18, wherein terminating comprises removing a cannula associated with cardiopulmonary bypass.

23. The method of claim 18, wherein terminating comprises closing the chest of the patient.

24. The method of claim 18, wherein terminating is conducted when the core body temperature is about 32° C.–34° C.

25. The method of claim 18, wherein selectively adding comprises adding heat at an operator controlled rate.

26. The method of claim 18, wherein selectively adding heat further comprises:
determining the core body temperature; and
controlling the rate of heat transfer from the catheter to the blood in the blood flow path based on the determination of core body temperature.

27. The method of claim 18, wherein the catheter is placed in the central venous system of the patient.

28. The method of claim 18, wherein transferring comprises circulating in the catheter a heat exchange fluid having a temperature above the temperature of the blood in the blood flow path.

29. The method of claim 28, wherein circulating comprises:
inflating one or more balloons of the catheter; and
circulating the heat exchange fluid in the inflated one or more balloons.

* * * * *